United States Patent [19]

Lonky

[11] Patent Number: 5,179,938
[45] Date of Patent: Jan. 19, 1993

[54] APPARATUS FOR ENDOSCOPIC EXAMINATION OF BODY CAVITY USING CHEMILUMINESCENT LIGHT SOURCE

[75] Inventor: Neal M. Lonky, Yorba Linda, Calif.

[73] Assignee: The Trylon Corporation, Torrance, Calif.

[21] Appl. No.: 660,674

[22] Filed: Feb. 25, 1991

Related U.S. Application Data

[63] Continuation-in-part of Ser. No. 526,770, May 18, 1990, which is a continuation of Ser. No. 20,188, Feb. 26, 1987, abandoned, which is a continuation of Ser. No. 694,092, Jan. 23, 1985, abandoned, which is a continuation-in-part of Ser. No. 581,363, Feb. 17, 1983, abandoned.

[51] Int. Cl.⁵ .............................. A61B 1/06
[52] U.S. Cl. .......................... 128/18; 606/3; 606/14
[58] Field of Search .................... 128/3-9, 128/11, 13, 16-19; 43/4.5; 362/34, 170; 606/3, 13-16

[56] References Cited

U.S. PATENT DOCUMENTS

| | | | |
|---|---|---|---|
| 3,576,987 | 5/1971 | Voight | 240/2.25 |
| 3,769,968 | 11/1973 | Blount et al. | 128/17 |
| 3,789,835 | 2/1974 | Whitman | 128/18 |
| 4,248,214 | 2/1981 | Hannah et al. | 128/7 |
| 4,905,670 | 3/1990 | Adair | 128/18 |

Primary Examiner—Max Hindenburg
Attorney, Agent, or Firm—Blakely, Sokoloff, Taylor, Zafman

[57] ABSTRACT

The present invention is an apparatus for performing medical examinations in body cavities, and a method of performing such examinations. The apparatus has a chemiluminescent light source having particular wavelength characteristics made up of blue and green wavelengths, and preferably a smaller peak of red light. The apparatus permits improved screening of the mucosal surfaces of body cavities such as the vaginal, anal and oral cavities for a number of abnormalities including lesions, atypia, dysplasia, abnormal vascularization and abnormal discharge. The method of performing examinations using the apparatus is also described.

19 Claims, 3 Drawing Sheets

SPECTRAL OUTPUT CURVE

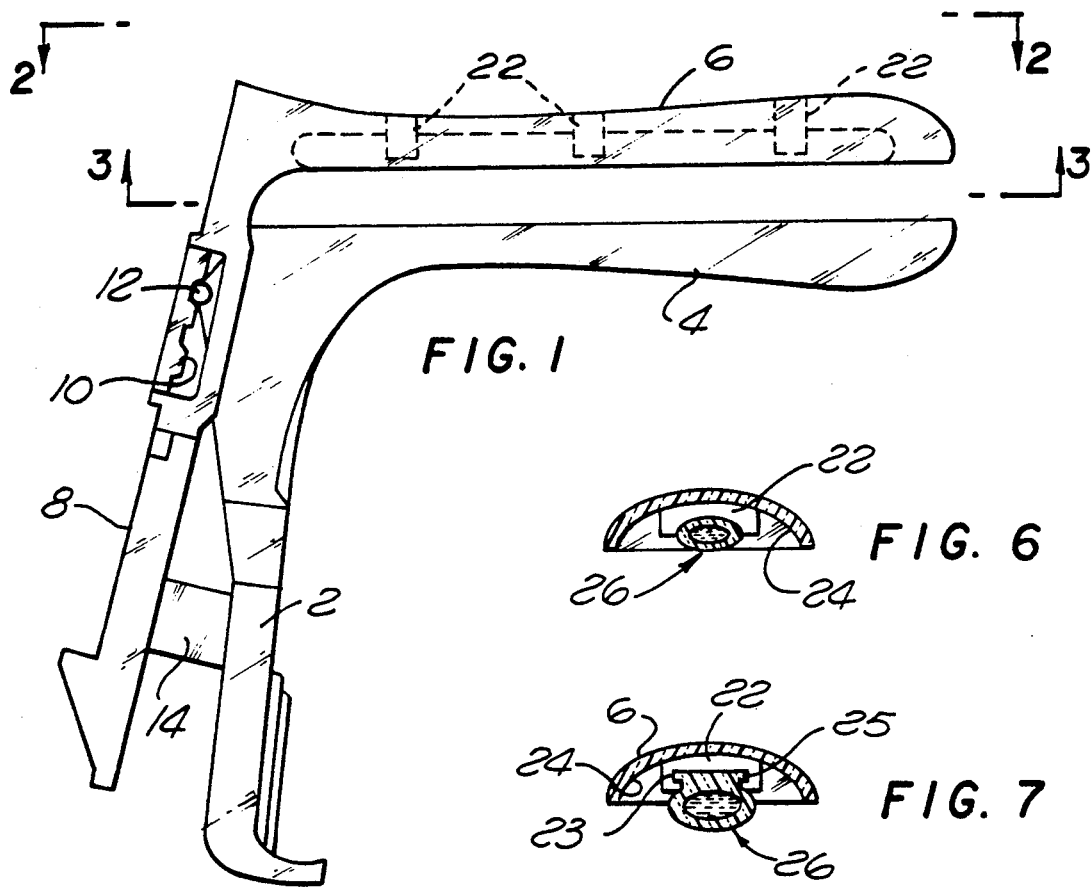
FIG. 1
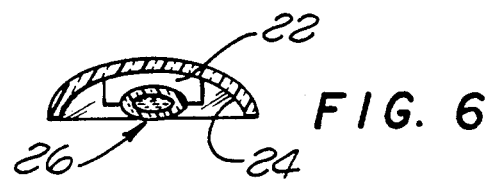
FIG. 6
FIG. 7
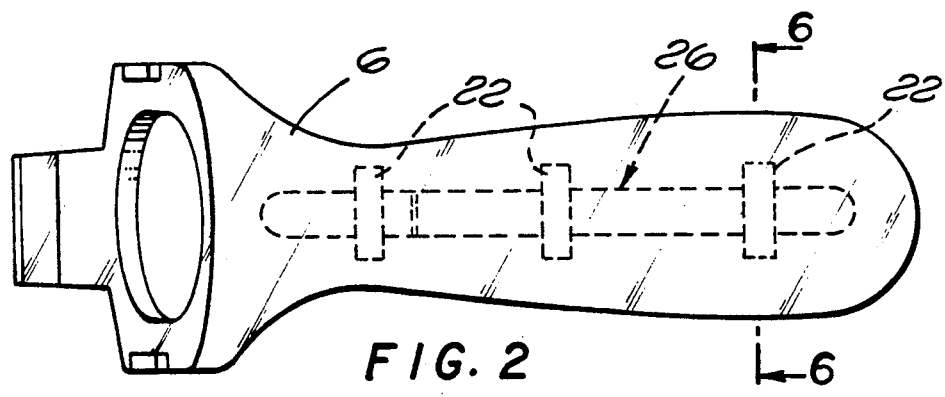
FIG. 2
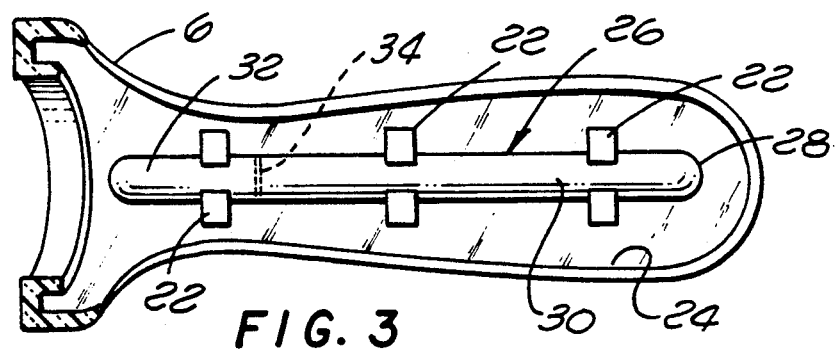
FIG. 3

APPARATUS FOR ENDOSCOPIC EXAMINATION OF BODY CAVITY USING CHEMILUMINESCENT LIGHT SOURCE

RELATED CASE INFORMATION

This application is a continuation in part of U.S. patent application Ser. No. 07/526,770, filed on May 18, 1990 pending, which is a continuation of application Ser. No. 07/020,188 filed on Feb. 26, 1987 and now abandoned, which is a continuation of application Ser. No. 06/694,092 filed on Jan. 23, 1985 and now abandoned which is a continuation in part of application Ser. No. 06/581,363 filed on Feb. 17, 1983 and now abandoned.

BACKGROUND OF THE INVENTION

1. Field of the Invention

This invention is in the field of medical devices and methods, and more particularly, directed to the field of endoscopes, such as speculae, anoscopes and sigmoidoscopes, and the like, and their light sources, and the use of speculae and other endoscopic instruments with particular light sources for diagnosis of various abnormalities, as well as for regular examinations. This invention also relates to a new method for performing vaginal exams to greatly improve the accuracy of detecting various disorders, and new devices for performing the improved exams.

2. Art Background

As used herein the term speculoscopy refers to an endoscopic procedure involving a visually magnified examination of a body cavity or cavities employing a diffuse, internal, chemiluminescent light source. It is a special type of endoscopy, generally suited for vaginal exams, although it may be employed in the examination of any body cavity.

The use of an endoscope for various medical diagnostic procedures is well known in the art. Many different types of endoscopes are known for such diagnostic procedures, as well as for retraction during various surgical procedures, and one type of device is disclosed in my copending U.S. patent application Ser. No. 07/526,770.

This patent application discloses an endoscopic instrument, such as a speculum, comprising a housing and a chemiluminescent light source attached thereto. The light source is comprised of an elongated sealed tube made of transparent or translucent material and having disposed therewithin a chemiluminescent material. The chemiluminescent light source transmits a diffused source of light throughout the cavity being observed. The chemiluminescent light source is attached to the instrument body by an attachment means disposed along the longitudinal axis of the instrument body. This chemiluminescent light source, while not specified in the application, has been an orange/yellow, also called amber, light having a wavelength profile as shown in FIG. 10. This device has been on sale for several years.

The chemiluminescent light source, in addition to providing a portable source of illumination of the body cavity, does so without producing any heat which could damage, or at least be uncomfortable to, the tissue in the body cavity which is being observed with the endoscopic instrument or by use of the speculum. Moreover, there is no requirement for any electrical source such as a power cord or batteries. This device also disburses light throughout the cavity being observed, rather than focuses light at a specified location.

With respect to many of such endoscopes comprising the chemiluminescent light source, the entire instrument, including the light source, may be disposed of after use. For other instruments, which are not disposable, those instruments may be sterilized, and the chemiluminescent light source disposed of and then replaced, to obtain a completely sterile device.

In view of the fact that the chemiluminescent light source does not require any electricity, the endoscope does not have to be connected to or powered by any electrical source and can be stored for substantial periods of time without any loss of function because until the chemiluminescent light source is activated by the combination of the two chemiluminescent components, there is no loss of function. On the other hand, batteries which are used in the operation of standard electrical lights which are used in many prior art devices, can deteriorate in function even when not in use over a period of time, particularly under adverse conditions such as high heat and/or humidity. Thus, the present invention is particularly useful in primitive locations where relatively high temperature and heat may be prevalent and long periods of storage may be required before the invention is used as an endoscope or speculum. Of course, the present invention does have some anticipated shelf life and may, at times be somewhat temperature sensitive.

Currently, a standard gynecological exam or gyn exam comprises the use of a speculum, a visual examination of the interior cavity and related structures, palpation of the pelvic region and a pap smear. The visual examination is typically performed using a gooseneck lamp or even a flashlight without any use of magnification, although magnification is certainly available in the medical field in other areas, such as microsurgery. There are several disadvantages to the current procedure.

First, because a projecting light source is used, the ability to visualize abnormalities or areas of concern is diminished since there is not evenly disbursed lighting and there may be shadows or glare which distort the appearance of the area. Second, because an external light source is used, the same problems occur. Third, because the light source is incandescent, it gets hot and cannot be placed too close to the patient without burning or uncomfortably heating the area being examined, or the area adjacent thereto. Finally, and of some concern, the various peaks of the wavelengths of the light (generally white light) is not the most advantageous for viewing the various abnormalities to be detected. If the abnormalities are not detected visually, they may be detected by the Pap smear. However, there has been an increasing amount of controversy surrounding the Pap smear, regarding the quality of the sampling taken and consequently the accuracy of the results, which are typically performed by an outside laboratory, rather than by the doctor himself, or even his staff under his supervision. Consequently, the false negative rate for Pap smears (indicating nothing wrong, when there is a problem) has been shown to be approximately 30%).

If abnormalities are detected, the patient is brought in a second time for a more detailed examination using a colposcope. This device is a binocular microscope which is placed near the patient. A bright light, (blue/green filtered white incandescent light) is supplied. The operator looks through the eyepieces of the colposcope much like looking through field glasses. This procedure is performed with a vaginal speculum or similar device in place. Some of the colposcopes have camera attachments for still picture photography.

If abnormalities are detected, the physician washes the area with 3-5% acetic acid and then exams the tissue for whitened areas after treatment. The acetic acid whitens tissue which is thickened, such as cancer cells. The physician also looks for clusters of blood vessels which may indicate new growth such as cancer.

The effectiveness of this colposcopy procedure in detecting abnormalities is believed to be approximately 85%, and this effectiveness is due in part to the greater amount of experience which physicians who utilize this procedure generally have. It should be noted, however, that the colposcope is difficult to use because of its size, weight and complexity. Accordingly, it is not available in all medical facilities. It is also very expensive and not at all portable.

Because colposcopy is a specialized procedure, requiring advanced and comprehensive training on very complicated and expensive apparatus, colposcopy is typically only performed on patients who have had an abnormal screening procedure (i.e. Pap smears or other indications). Such systems have been shown to be useful in the confirmation of Pap test results, as well as in other diagnostic procedures. Various forms and variations of colposcopes are disclosed in U.S. Pat. Nos. 3,994,288, 4,134,637, 4,232,933, 4,652,103 and 4,905,670.

One prior art colposcope is described in Adair, U.S. Pat. No. 4,905,670, which discloses an apparatus which includes a vaginal speculum having a first fixed blade, a second blade mounted for pivotal movement toward and away from the fixed blade and spring means normally urging the second blade toward the fixed blade. The apparatus also includes a video camera mounted on one of the blades for viewing the cervix, means providing light to the cervix, means for focusing the camera on a selected site on the cervix and means for providing a signal from the camera to a video screen for viewing the cervix and identifying lesions thereon. The light providing means can include a light carrier on the track for providing light to the cervix. In addition, means is provided for selecting light for illumination of the cervix at any one of a range of light frequencies. This can be broad frequency light, monochromatic light or possibly even laser light for illumination. A particularly useful light frequency has been found to be from 200 nm through 1100 nm. A suitable means for stepping sequentially through the frequencies is a monochromator. The monochromator converts light from a light source to a single frequency at an output in the form of a rectangular slit. A light carrier is provided which includes a bundle of optical fibers having a first end in a form of a rectangular collar for receiving the output from the monochromator and a circular collar at the other end for directing a round column of light onto the cervix.

Regarding the speculae which have been used over the years, the following are representative of those having attachments and designs which are pertinent to the subject invention:

Casaneda U.S. Pat. No. 4,210,133 discloses a vaginal speculum having a microscope mounted thereon which has a light source for illumination and is longitudinally adjustable for focusing.

VanDerBel U.S. Pat. No. 4,597,383 discloses a vaginal speculum having optical fiber illumination means attached thereto.

Burgin U.S. Pat. No. 4,638,792 has an adjustable speculum with an incorporated light system.

Walsh U.S. Pat. No. 4,619,248 discloses a light attachment for a speculum.

Wider et al. U.S. Pat. No. 4,562,832 illustrates in FIG. 6 a fiberoptic light pipe installed in the lower jaw of the vaginal speculum.

Burgin U.S. Pat. No. 4,502,468 has an adjustable speculum with an incorporated lighting system.

Whitman U.S. Pat. No. 3,789,835 discloses an illuminating attachment for vaginal speculum.

Stafl U.S. Pat. No. 4,300,570 discloses a diagnostic method including projecting and magnifying an image of a cervix photographed by a device disposed on a speculum.

Walden et al. U.S. Pat. No. 3,037,505 discloses a speculum with a spray tube carried by a jaw of the speculum.

Tanikawa et al. U.S. Pat. No. 4,461,558 discloses an endoscopic photographing apparatus applicable to all types of endoscopes and uses therefor.

Toyota et al. U.S. Pat. No. 4,697,210 discloses an endoscope for observing the interior of a cavity in a human body with the image displayed on a TV screen.

The last two patents are representative of many observation techniques available for use with endoscopes.

The present invention overcomes the drawbacks of the prior art by providing an endoscopic examination and viewing system that is compact, portable, disposable, shadowless, economical and efficient. The present invention also comprises a method of detection of various cellular abnormalities which is quicker, easier, more economical, simpler, more compact, and which can be performed in an office setting without the use of prior art colposcopy equipment.

SUMMARY OF THE INVENTION

The present invention is an endoscopic instrument comprising a housing and a chemiluminescent light source attached thereto. In addition to the light source of the present invention, the endoscopic instrument may have optical enlargement lenses and means for spreading or otherwise retracting a portion of the cavity to be observed in order to place the diffused light within the cavity and to permit observation of the tissue therein.

The chemiluminescent light emits light in a particular frequency range obtained by the combination of particular chemiluminescent materials commercially distributed by American Cyanamid, Inc. (Wayne, N.J.) which, sometimes referred to as a cyalume light. The specific frequency peaks of the preferred embodiment of present invention are at about 450 nm and 550 nm and a smaller peak in the red region at about 600 nm which in combination create, emanate or elicit a white light.

The chemiluminescent light source is provided in a sealed container, as described in the above-referenced copending patent application, or otherwise, such that the chemicals can be easily mixed without having to specially handle or mix the chemicals by hand. Several different structures are proposed in the copending application for this purpose including, but not limited to, providing a frangible container inside a flexible container so that the flexible container can be manipulated to break the container and allow the components to mix, and separating the components in a container by a breakable wall and use a plunger or other device or method to break the wall to allow the components to mix.

The shape of the container can be any conventional, or nonconventional shape, and the size of the container is preferably large enough to contain a sufficient amount of chemiluminescent material to light the interior of the cavity being examined, or at least a sufficient to provide light for the portion of said cavity to be examined. The light source should be capable of being disposed within the cavity adjacent the area of the cavity to be examined. The diameter or width of the light source is adapted to be disposed on or in the endoscope if such arrangement is used. Preferably the light source is an elongated tube which can be inserted one end first into a cavity. There is preferably sufficient chemiluminescent material of proper reactivity for the light to remain lit for at least 2 minutes and as much as 30 minutes, although longer chemiluminescent light generation would certainly provide an operative system, and shorter duration may also work for certain types of examinations.

In the preferred embodiment, the chemiluminescent light source is attached to one of the dilator blades of a clear plastic speculum or other endoscope with a means for opening and spreading the cavity to be observed. With the clear plastic speculum, the light transmits through the blades to illuminate the entire cavity being observed. However the speculum does not have to be clear and solid metal speculae may be used as well. The light source may be inserted directly into the cavity or may be disposed outside the cavity, the light being directed inward into the cavity by means of mirrors or fiber optic elements. Preferably, though, the chemiluminescent light source provides direct lighting to the examination surface in order to take advantage of the diffuse, non-directed light emanating from the container of the chemiluminescent material.

The endoscope may contain a magnification means for magnifying the cavity under illumination by the invented light in order to enlarge the examining practitioner's view of the surface. Various configurations of the magnification means may be employed including but not limited to a utilizing a separate magnification means and light source, or attaching the magnification means to the light source.

The present invention also comprises a method of detection of various medical disorders by means of providing a transparent or translucent sealed container comprising separated chemiluminescent materials which when mixed together emit a chemiluminescent light in the range of blue-white, green white and green-blue-white, mixing the chemiluminescent materials together to cause said chemiluminescent materials to emit said light, directing said light to a surface of a body cavity and examining said lit surface. Preferably, the surface of the cavity to be examined is treated prior to examination with a composition which enhances the visualization of various tissue, such as by coating the surface with dilute aqueous acetic acid. Additionally a magnification means or scope may be used to enhance the examination.

In the primary embodiment of the present invention, as it relates to vaginal and cervical examinations, the presently invented method comprises coating the vaginal and/or cervical mucosal membranes with a solution of 1% to 10% acetic acid, mixing the aforesaid chemiluminescent materials together, attaching the container containing said chemiluminescent materials to a speculum, inserting the speculum into the vaginal passage so that chemiluminescent is directed onto the surface, providing a magnification means for magnifying the surface of the cavity and examining the surface for the occurrence of non-normal tissue. The speculum is preferably, but not necessarily, made of clear material so that the chemiluminescent light is transmitted through speculum and there will be no or minimized shadows in the cavity,

BRIEF DESCRIPTION OF THE DRAWINGS

FIG. 1 is a side view of one embodiment of the present invention wherein the speculum is the endoscopic instrument FIG. 2 is a top plan view of the upper dilator means of the present invention as taken through lines 2—2 in FIG. 1.

FIG. 3 is a bottom up view of the upper dilator means of the present invention as taken through lines 3—3 in FIG. 1.

FIG. 6 is a sectional view of the upper dilator blade of the embodiment of the present invention as shown in FIG. 2 and taken through lines 6—6 of FIG. 2.

FIG. 7 is a sectional view of an alternate embodiment of the upper dilator blade to the embodiment shown in FIG. 6.

DETAILED DESCRIPTION OF THE INVENTION

Figure 4:
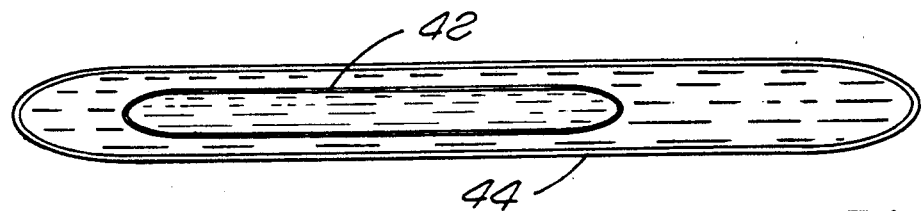
FIG. 4 is an illustration of the preferred embodiment of the chemiluminescent light source of the present invention.

The present invention is a method and apparatus for the examination of body cavities endoscopically which increases the likelihood of detection of many visually observable abnormalities, such as lesions, irregular vasculature, exophytic regions, ulcerations and other atypias of the cervix, vaginal cavity and other body cavities, as well as discharges. The apparatus can take on any shape which may be usefully employed by insertion into the cavity to be examined, and generally a cylindrical shape corresponding to the shape and size of the cavity to be observed, although it is obviously smaller in diameter than the cavity in order to provide an area to enable the physician to view the tissue to be examined. Much of the detailed description which follows relates specifically to a vaginal speculum. However, it will readily be appreciated that the invention not only is suitably employed in all speculae, but also is capable of serving as a light source for all endoscopic instruments for illumination and examination of the several body cavities including but not limited to the anal and oral cavities.

In FIG. 1, one embodiment of the present invention is shown in which the chemiluminescent light source is attachable to a speculum. Specifically, the instrument shown in FIGS. 1-3 and 6 and 7 comprises a handle 2 connected to a lower dilator blade 4, and upper dilator blade 6 having a second handle 8. Handle 8 is operatively connected to handle 2 in a slideably adjustable manner by means of slot 10 in handle 8 which engages around pivot pin 12 on handle 2. The upper dilator blade of the speculum is provided with extending locking tab 14, by means of which the physician can hold in position the remote ends of the two dilator blades separated within the vaginal cavity as the blades are pivoted with respect to one another at pivot pin 12. A plurality of rib-like members 22 are located on the interior surface of upper dilator blade 6 intermediate the two dilator blades and have a channel 24 therein adapted to receive and retain therein, in a releasable, snap-fit, a medical examination light 26.

Medical examination light 26 produces light by chemiluminescent means and has an hermetically sealed, flexible light transmitting tube 28 with at least two compartments 30 and 32 separated by a breakable wall 34 with a chemiluminescent component in each compartment. In one compartment is the fluorescer component and in another is the activator component. Mixing of the components produces the chemiluminescent effect, as is well-known. Tube 28 has a cross-sectional shape adapted to be received and retained in channel 24 in a releasable, snap-fitting engagement. Once in position and activated as described, medical examination light 26 directs its light intermediate the two dilator blades in their extended position to illuminate the cavity for the examining physician.

FIGS. 6 and 7 show two alternative retaining means for retaining the light in the speculum, which retaining means may be applied to any endoscopic instrument for use in accordance with the present invention. In FIG. 6 the upper dilator blade 6 has a retaining means comprising a snap fit member 22 shaped to engage and retain the light 26 within the channel 24. In FIG. 7, the retaining means 22 has a slot 23 which retains a flange 25 attached to the light 26.

As shown in FIG. 4, the light is comprised of two compartments as described above. The inner compartment 42 is breakable, such as a frangible ampoule, and contains one of the components, either the activator or the fluorescer. The outer compartment 44 is partially or fully flexible, but is sturdy enough to resistant being cut or broken when the ampoule is broken. It contains the other component.

Figure 5:
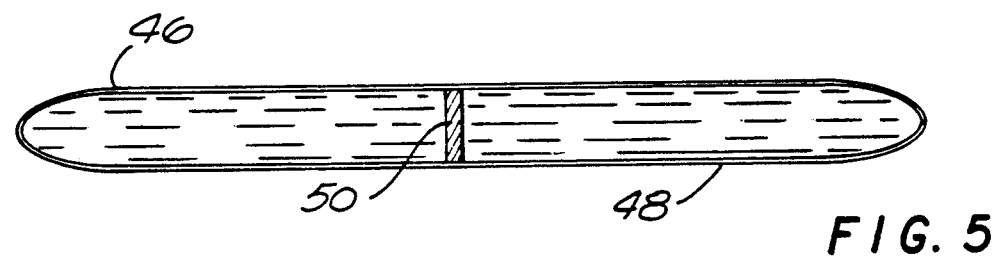
FIG. 5 is an illustration of an alternative embodiment of the chemiluminescent light source of the present invention.

As shown in FIG. 5 the compartments 46 and 48 are side by side with a breakable membrane 50 disposed between the two compartments to prevent mixture of the materials in the compartments until the membrane is broken.

It will be appreciated by a person of skilled in the art that many other configurations could be provided to provide to separate the two components of the fluorescent material without departing from the spirit and scope of the present invention.

Figure 8:
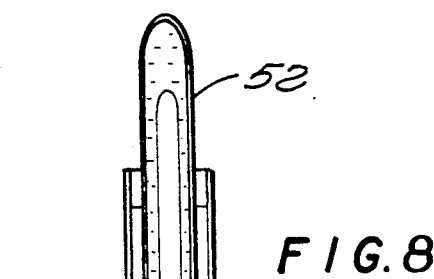
FIG. 8 is a side view of a chemiluminescent light source disposed in a wand endoscope of the present invention.
Figure 9:
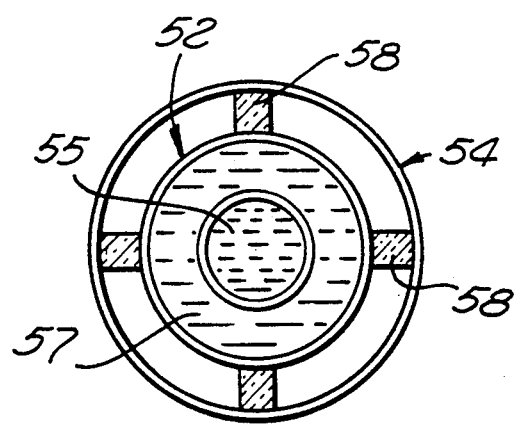
FIG. 9 is an enlarged cross sectional view of the invention shown in FIG. 8 taken through lines 9—9 thereof.

FIG. 8 depicts a light source 52 of the present invention disposed in an endoscopic wand 54. FIG. 9 shows a cross section of the light source in the wand with showing the inner compartment 55 within the outer compartment 57 and the entire light 52 being retained in the wand 54 by a plurality of detents 58. The light source may alternatively be held in place by adhesive, tight fit, snap-fit or any other retaining means known in the art.

Figure 10:
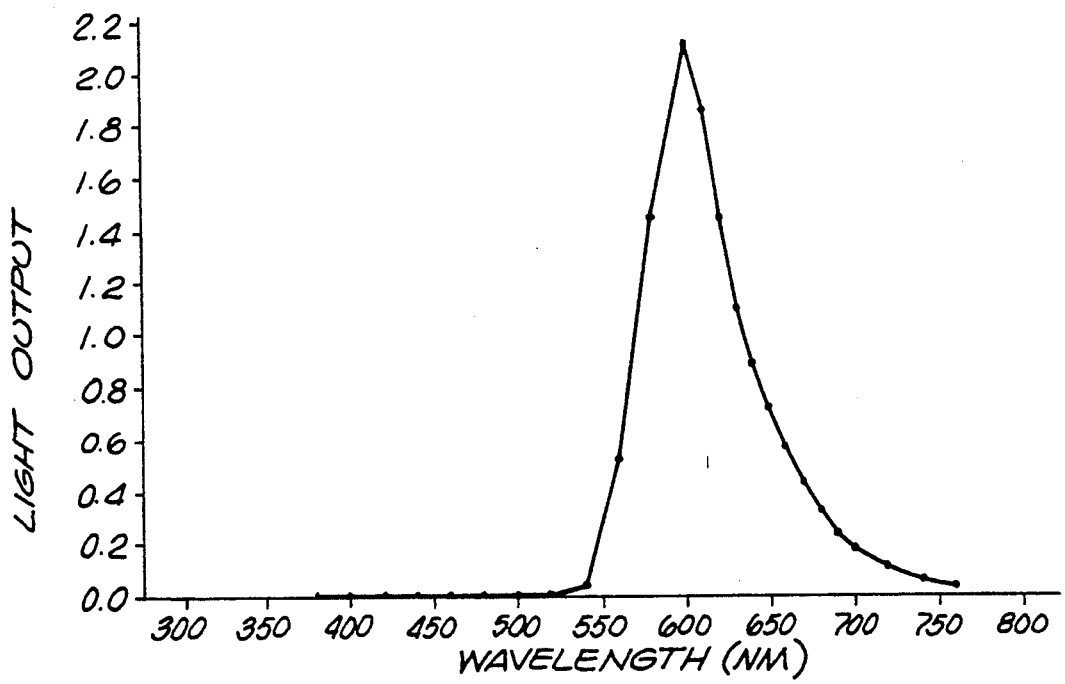
FIG. 10 is a graph showing the profile of the wavelength of light from the prior art amber chemiluminescent light source.
Figure 11:
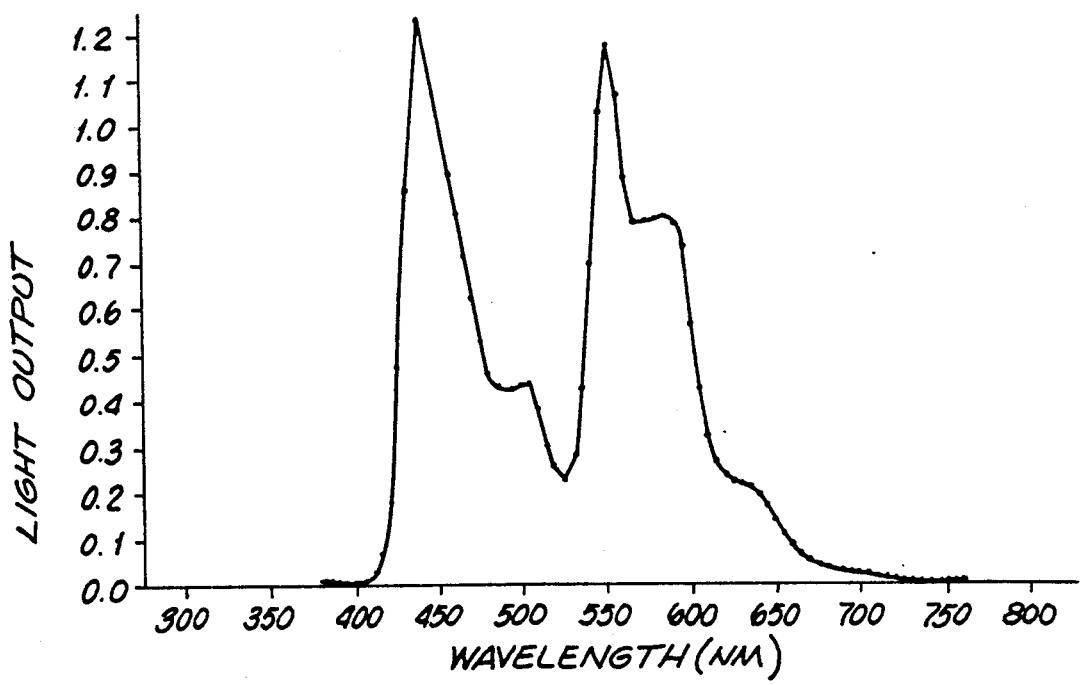
FIG. 11 is a graph showing the profile of the wavelength of light from the present invention chemiluminescent light source.

FIG. 10 shows the wavelength scan of the prior art amber light. As can be seen there is a single peak at about 600 nm. In the preferred embodiment of the present invention, the wavelength profile is as shown in FIG. 11. In FIG. 11, there are two major peaks at about 450 nm and 550 nm, and a minor peak at about 580 nm. This corresponds to green and blue light for the major peaks and red light for the minor peak. The combination forms a chemiluminescent white light source with the advantages described herein. Such chemiluminescent light source is available from American Cyanimid (Wayne, N.J.)

The method of the present invention involves inspection of the surface to be examined using the invented endoscopic light comprising a chemiluminescent light source in the green and blue wavelength ranges described herein. Generally, the method and apparatus of the present invention are designed to provide improved viewing of visual detectable anomalies in body cavities, such as vaginal exams, which together with necessary follow-up confirmatory diagnostic tests, is intended to provide significantly more accurate detection of problems in the region to be examined. Among the various anomalies which may be more accurately detected by the procedure described herein are the following:

Acetowhite lesion, which are thickened mucosal epithelium which reflect light upon examination following application of dilute acetic acid, and appear lighter or white when compared to the surrounding normal mucosa Leukoplakia, which is thickened mucosal epitherlium which reflect light upon examination following application of dilute acetic acid, and appear lighter or white when compared to the surrounding normal mucosa; this appearance is not dependent upon the application of acetic acid.

Condyloma/Human Papilloma Virus/Genital Warts are wart-like verrucous, papillated mucosal lesions or growths which appear lighter or white after the application of dilute acetic acid (acetowhite).

Dysplasia, Intra-Epithelial Neoplasia and Frank Carcinoma is recognized by one or more lesions which may appear ulcerated or thickened, acetowhite, erythematous, may be raised or associated with an abnormal shape or pattern of microvascular such as punctated, mosaic like (mosaicism), erratic web-like shaped, or any combination thereof.

Mucopurulence is a yellow white exudate or discharge often found in cases of infectious microorganisms such as Chlamydia which elicit a leukocytic reaction.

Ulceration is recognized as a lesion of the mucosal, similar to Herpes Simplex Virus lesions, but not having the same diagnostic characteristics.

Abnormal vascularization which is indicative of possible cancerous or precancerous regions, and is recognized by the presence of excessive vascularization near the surface of the examined tissue.

In order to properly screen patients for the above-mentioned problems, as well as many others, the physician first activates the chemiluminescent light source by breaking the membrane or inner ampoule, and then attaches the ligth source to an endoscope, such as the speculum or wand described above. The physician then coats, sprays or paints the area to be examined with 1 to 10% acetic acid, and preferably 3 to 5% acetic acid. The cavity is then examined first under normal 1× magnification, and then under higher magnification in the range of up to 10× and preferably 3.5 to 5×. Any necessary biopsies may be taken if the observation warrants follow-up testing.

In a recent 600 person perspective multicenter study, the use of the standard current procedure of a typical speculum with observation using a standard goose neck incandescent lamp and a Pap smear, showed approximately a 35% false negative rate for the detection of cervical cancer and its precursors. The additional use of the present invention decreased the false negative rate to approximately 10%. There was no significant difference between the false positive rates for each of the tests.

The purpose of the present invention is to provide a tool to allow physicians to more accurately screen patients for various diseases, and to provide an indication of which patients require follow-up examinations. This inventive procedure can be performed in the doctor's office with the patient present, without requiring the patient to wait for the results of the Pap smear which is usually performed over several days to a week at an outside laboratory. Thus, any follow up may be accomplished or discussed immediately following detection of the problem, alleviating excessive patient concern. It also alleviates the problems which have been recognized relating to the tests being performed by outside laboratories without any control by the patient's personal physician. Further, as clearly established above, the results of the comparison of the two procedures establishes the accuracy of the present invention over the prior art method.

The present invention is not intended as a substitute for routine Pap smears; rather, it is intended to be used in conjunction with such tests to increase the accuracy of the screening procedure, adding a sensitive visual screening procedure to the existing cytological laboratory screening.

It will be obvious to a person of ordinary skill in the art that the present invention is not limited in its design or application to specific embodiments disclosed herein. Rather, the present invention is intended to encompass all of the embodiments disclosed and suggested herein as defined by the claims appended hereto and any equivalents thereof.

What is claimed is:

1. An apparatus for the detection of various internal disorders in a body cavity which are visually detectable endoscopically, said apparatus comprising a liquid impervious light transmitting body containing therein a chemiluminescent light source for creating a chemiluminescent light in the spectrum comprising at least blue and green wavelengths of light, and combinations thereof, said light transmitting body being sized to be disposed within the cavity to be examined, said light source creating a diffused light which illuminates said body cavity without producing any substantial shadows and wherein said spectrum allows enhanced visualization of said various internal disorders.

2. The apparatus of claim 1 wherein said chemiluminescent material comprises two reactive materials separated from each other by a breakable means.

3. The apparatus of claim 1 wherein said chemiluminescent material is characterized as having a light output having spectral peaks at about 450 and 550 nanometers.

4. The apparatus of claim 3 wherein the light output from said chemiluminescent material is further characterized as having a spectral peak at about 580 nanometers.

5. The apparatus of claim 1 wherein the light from said chemiluminescent material is characterized as having spectral peaks at 450, 550 and 580 nanometers.

6. The apparatus of claim 1 wherein the light from said chemiluminescent material is blue, green and a lesser amount of red light forming a generally white light source.

7. The apparatus of claim 1 further comprising an endoscopic instrument means adapted to be inserted into said cavity and non-removably retain said chemiluminescent light source.

8. An apparatus for the detection of various internal medical disorders in a body cavity which are visually detectable endoscopically said apparatus comprising a liquid impervious light transmitting body containing therein a chemiluminescent light source for creating a chemiluminescent light in the spectrum of blue, green and red wavelength light, said light transmitting body being sized to be disposed within the cavity to be examined, said light source creating a diffused light which illuminates said body cavity without producing any substantial shadows and wherein said spectrum allows enhanced visualization of said various internal disorders.

9. An endoscopic instrument for use in examining a body cavity, comprising:
   a body comprising a handle means and a means for insertion into said body cavity;
   a chemiluminescent light source comprising a light transmitting body which produces diffuse light and chemiluminescent materials disposed within said light transmitting body in at least two separate compartments, wherein said chemiluminescent material is characterized as producing light have a spectral output in the blue, green and red wavelengths, and whereby the intermixing of said materials causes said materials to chemiluminescence thereby diffusing said light in all directions throughout, wherein said spectral output of said light allows enhanced visualization of various internal disorders in said body cavity; and
   an attachment means disposed on said insertion means for attaching said chemiluminescent light source thereto,
whereby said light source provides diffuse illumination of said body cavity without any substantial shadows and without producing any heat which could damage tissue in said body cavity.

10. The endoscopic instrument of claim 9, wherein said attachment means removably attaches said chemiluminescent light source to said instrument body.

11. The endoscopic instrument of claim 10 wherein said attachment means comprises a plurality of rib-like means which capture said body of said light source in a snap-fit manner.

12. The endoscopic instrument of claim 10 wherein said attachment means comprises a two sided adhesive means.

13. The endoscopic instrument of claim 9 wherein said instrument is a speculum.

14. The endoscopic instrument of claim 9 wherein light has spectral output peaks at wavelengths of 450 nm, 550 nm and 580 nm.

15. A speculum for use in examining a body cavity, comprising:
   a body comprising a pair of dilator blades;

an attachment means disposed on at least one of said dilator blades for attaching said chemiluminescent light source thereto, a chemiluminescent light source, said chemiluminescent material which produces blue and green wavelength light, and comprising an hermetically sealed flexible light transmitting tube with at least two compartments separated by a breakable wall, with a chemiluminescent component in each of said compartments, said tube adapted to be received and retained by said attachment means and to direct its light intermediate said dilator blades in their extended position, wherein said blue and green wavelength light allows enhanced visualization of various internal disorders in said body cavity;

whereby said light source provides diffuse illumination of said body cavity without any substantial shadows and without producing any heat which could damage tissue in said body cavity.

16. The speculum of claim 15 wherein said attachment means comprises a plurality of rib-like means which capture said body of said light source in a snap-fit manner.

17. The speculum of claim 15 wherein said attachment means comprises a two sided adhesive means.

18. A speculum for use in examining a body cavity, comprising:

a body comprising a pair of adjacent dilator blades;

an attachment means comprising at least one rib-like member on the surface of at least one of said dilator blades intermediate to said dilator blades, said rib-like member having a channel therein adapted to receive and retain therein, in a releasable snap-fit, said chemiluminescent cold light source, and a chemiluminescent light source being characterized as producing light having wavelength peaks at 450, 550 and 580 nm and comprising an hermetically sealed flexible light transmitting tube with at least two compartments separated by a breakable wall, with a chemiluminescent component in each of said compartments, said tube adapted to be received and retained by said attachment means and to direct its light intermediate said dilator blades in their extended position, wherein said wavelength peaks of said light allow enhanced visualization of various internal disorders in said body cavity, whereby said light source provides diffuse illumination of said body cavity without any substantial shadows and without producing any heat which could damage tissue in said body cavity.

19. A medical examination light secured to a speculum of the type having a body and a plurality of dilator members extending from said body for use in examining a body cavity, said light comprising: a chemiluminescent cold light means adapted to be secured to one of said dilator members and to direct its light intermediate to said dilator members when disposed in a spaced-apart arrangement, said chemiluminescent light source emitting white light formed of blue, green and red wavelengths, said wavelengths of said light allowing enhanced visualization of various internal disorders in said body cavity, and a securement means adapted to secure said chemiluminescent cold light means to said dilator member, whereby said chemiluminescent cold light source provides diffuse illumination of said body cavity without any substantial shadows and without producing any heat which could damage tissue in said body cavity.

* * * * *